United States Patent [19]

Wada et al.

[11] Patent Number: 5,081,244
[45] Date of Patent: Jan. 14, 1992

[54] PYRIMIDINE DERIVATIVES, PROCESSES FOR THEIR PRODUCTION, AND HERBICIDAL METHOD AND COMPOSITIONS

[75] Inventors: Nobuhide Wada, Kakegawa; Shoji Kusano, Hamamatsu; Yasuhumi Toyokawa, Tokyo, all of Japan

[73] Assignees: Kumiai Chemical Industry Co., Ltd.; Ihara Chemical Industry Co., Ltd., both of Tokyo, Japan

[21] Appl. No.: 454,937

[22] Filed: Dec. 22, 1989

Related U.S. Application Data

[62] Division of Ser. No. 287,050, Dec. 21, 1988, Pat. No. 4,906,285.

[30] Foreign Application Priority Data

Dec. 22, 1987 [JP] Japan .................. 62-324964

[51] Int. Cl.$^5$ .......................................... C07D 403/00
[52] U.S. Cl. .................................................. 544/296
[58] Field of Search .......................................... 544/296

[56] References Cited

U.S. PATENT DOCUMENTS 4,248,619  2/1981  Serban et al. ................. 544/296

Primary Examiner—Jane T. Fan
Assistant Examiner—Raymond Covington
Attorney, Agent, or Firm—Oblon, Spivak, McClelland, Maier & Neustadt

[57] ABSTRACT

A pyrimidine derivative having the formula:

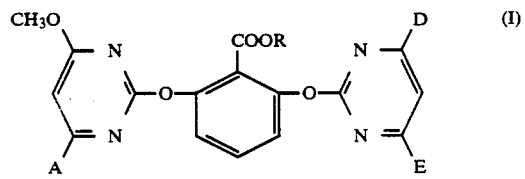

wherein R is hydrogen atom, $-CH_2CH_2S(O)_nR_1$ (wherein $R_1$ is a lower alkyl group, and n is an integer of from 0 to 2) or

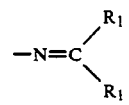

(wherein each $R_1$ is a lower alkyl group), A is a chlorine atom or a methoxy group, and each of D and E which may be the same or different, is a hydrogen atom, a halogen atom, a lower alkyl group, a lower alkoxy group or a halogen-substituted lower alkoxy group, or a salt thereof.

1 Claim, No Drawings

PYRIMIDINE DERIVATIVES, PROCESSES FOR THEIR PRODUCTION, AND HERBICIDAL METHOD AND COMPOSITIONS

The present invention relates to novel pyrimidine derivatives or their salts, processes for their production, herbicidal compositions containing them, and a herbicidal method for applying them.

U.S. Pat. Nos. 4,248,619 and 4,427,437 and Agr. Biol. Chem., Vol. 30, No. 9, p.896 (1966) disclose that 2-phenoxypyrimidine derivatives have herbicidal activities.

However, the compounds disclosed in these references have a drawback that their herbicidal activities are inadequate.

The present inventors have conducted extensive research on pyrimidine derivatives with an aim to develop a compound having more excellent herbicidal activities, and as a result, have found that the compounds of the present invention having substituents introduced at specific positions of the pyrimidine and benzene rings of phenoxypyrimidine derivatives, exhibit excellent herbicidal effects against perennial weeds as well as annual weeds, and at the same time, they have a high level of safety to crop plants, particularly to rice and wheat.

Namely, as compared with the compounds disclosed in U.S. Pat. No. 4,248,619, the compounds of the present invention are superior in the herbicidal activities, particularly in the herbicidal activities in post emergence treatment. Further, the compounds of the present invention have a wide herbicidal spectrum, and they are capable of controlling at a relatively low dose weeds such as common cocklebur (*Xanthium strumarium*), morningglory (*Ipomoea spp*) and purple nutsedge (*Cyperus rotundus*) which are usually hardly controlable. Furthermore, the compounds of the present invention have a high level of safety to rice in view of the low dose required for effectively controlling weeds.

The present invention has been accomplished on the basis of thes discoveries.

The present invention provides a pyrimidine derivative having the formula:

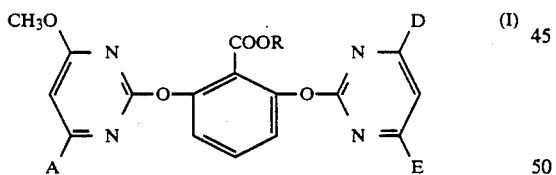

wherein R is a hydrogen atom, $-CH_2CH_2S(O)_nR_1$ (wherein $R_1$ is a lower alkyl group, and n is an integer of from 0 to 2) or

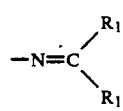

(wherein each $R_1$ is a lower alkyl group), A is a chlorine atom or a methoxy group, and each of D and E which may be the same or different, is a hydrogen atom, a halogen atom, a lower alkyl group, a lower alkoxy group or a halogen-substituted lower alkoxy group, or a salt thereof.

The present invention also provides a herbicidal composition comprising a herbicidally effective amount of a pyrimidine derivative of the formula I or a salt thereof, and an agricultural adjuvant.

Further, the present invention provides a method for killing weeds which comprises applying a herbicidally effective amount of a pyrimidine derivative of the formula I or a salt thereof to a locus to be protected.

The present invention also provides a process for producing a pyrimidine derivative of the formula I, which comprises reacting a 2,6-dihydroxybenzoic acid ester having the formula:

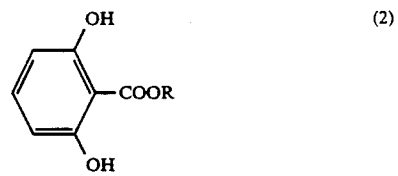

wherein R is as defined above, with a 2-substituted 4,6-disubstituted pyrimidine having the formula:

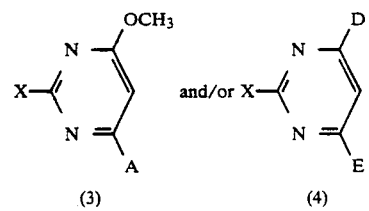

wherein A, D and E are as defined above, and X is a halogen atom, an alkylsulfonyl group or a benzylsulfonyl group, in the presence of a base.

Further, the present invention provides a process for producing a 2,6-bis[(4,6-disubstituted pyrimidin-2-yl)oxy]benzoic acid having the formula:

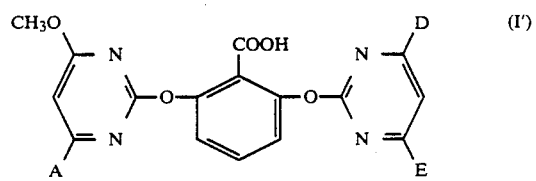

wherein A, D and E are as defined above, which comprises subjecting a compound having the formula:

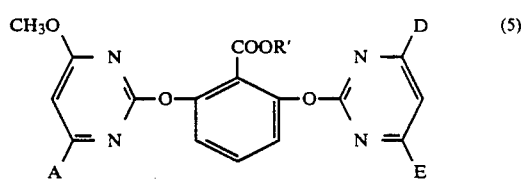

wherein A, D and E are as defined above, and $R_1$ is a carboxyl-protecting group selected from the group consisting of a lower alkylthioethyl group, a methoxybenzyl group and a trimethylsilylethyl group, to hydrolysis, hydrogenation or a reaction for removal of the carboxyl protecting group.

Furthermore, the present invention provides a process for producing a compound having the formula:

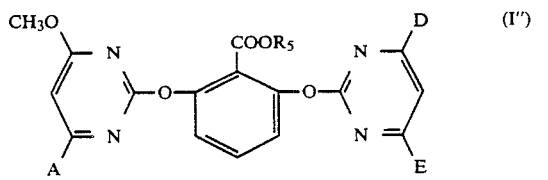

wherein A, D and E are as defined above, and $R_5$ is —$CH_2CH_2SR_1$ (wherein $R_1$ is a lower alkyl group) or

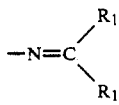

(wherein each $R_1$ is a lower alkyl group), which comprises esterifying a 2,6-bis[(4,6-disubstituted pyrimidin-2-yl)oxy]benzoic acid having the formula:

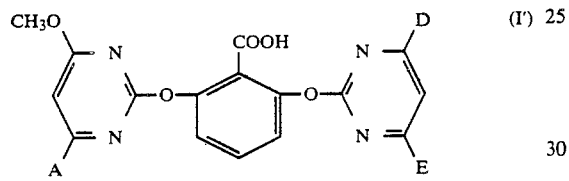

wherein A, D and E are as defined above, with an alkylating agent or with an alcohol.

Now, the present invention will be described in detail with reference to the preferred embodiments.

In the formula I, the lower alkyl group for each of $R_1$, D and E is preferably a $C_1$–$C_4$ alkyl group, the lower alkoxy group for each of D and E is preferably a $C_1$–$C_4$ alkoxy group, and the halogen-substituted lower alkoxy group is preferably a halogen-substituted $C_1$–$C_4$ alkoxy group.

Each of D and E which may be the same or different is preferably a hydrogen atom, a methoxy group or an ethoxy group, more preferably a hydrogen atom or a methoxy group. Particularly preferred is a compound of the formula I wherein A is a methoxy group, and each of D and E is a methoxy group.

In the formula I, R is preferably hydrogen atom, —$C_2H_4SCH_3$, —$C_2H_4SC_2H_5$, —$C_2H_4SOC_2H_5$ or —$C_2H_4SO_2C_2H_5$.

The salt of the pyrimidine derivative of the formula I may be an alkali metal salt, an alkaline earth metal salt, a transition metal salt or an organic ammonium salt. Particularly preferred is a triethanolamine salt, a diethanolamine salt, an ammonium salt, a sodium salt, a potassium salt or a calcium salt.

Now, typical examples of the compound of the present invention will be presented in Table 1. Compound Nos. given in the Table will be referred to in the subsequent description in the specification.

TABLE 1

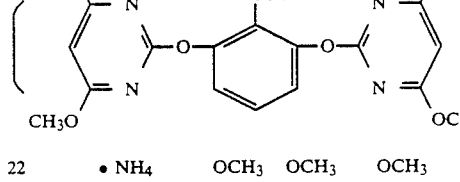

| No | R | A | D | E | Melting point (°C.) of refractive index |
|---|---|---|---|---|---|
| 1 | H | $OCH_3$ | $OCH_3$ | $OCH_3$ | 148–150 |
| 2 | $C_2H_4SCH_3$ | $OCH_3$ | $OCH_3$ | $OCH_3$ | $n_D^{20}$ 1.5706 |
| 3 | $C_2H_4SC_2H_5$ | $OCH_3$ | $OCH_3$ | $OCH_3$ | 76–79 |
| 4 | $C_2H_4SOC_2H_5$ | $OCH_3$ | $OCH_3$ | $OCH_3$ | 89–90 |
| 5 | $C_2H_4SO_2C_2H_5$ | $OCH_3$ | $OCH_3$ | $OCH_3$ | 92–96 |
| 6 | H | $OCH_3$ | Cl | $OCH_3$ | 150–152 |
| 7 | H | $OCH_3$ | $CH_3$ | $CH_3$ | 174–177 |
| 8 | H | $OCH_3$ | H | H | 120–125 |
| 9 | H | $OCH_3$ | Cl | $CH_3$ | 133–136 |
| 10 | H | $OCH_3$ | $CH_3$ | $OCH_3$ | 150–152 |
| 11 | H | $OCH_3$ | H | $OCH_3$ | 132–135 |
| 12 | H | Cl | Cl | $OCH_3$ | 149–150 |
| 13 | H | $OCH_3$ | H | $CH_3$ | 153–157 |
| 14 | H | $OCH_3$ | $OC_2H_5$ | $OC_2H_5$ | 143–144 |
| 15 | H | $OCH_3$ | $OCHF_2$ | $OCHF_2$ | 127–130 |
| 16 | H | $OCH_3$ | H | Cl | 83–88 |
| 17 | • $NH_3C_3H_7$-i | $OCH_3$ | $OCH_3$ | $OCH_3$ | 99–102 |
| 18 | • Na | $OCH_3$ | $OCH_3$ | $OCH_3$ | 235–237 |
| 19 | • $HN(C_2H_4OH)_3$ | $OCH_3$ | $OCH_3$ | $OCH_3$ | 103–110 |
| 20 | • $H_2N(C_2H_4OH)_2$ | $OCH_3$ | $OCH_3$ | $OCH_3$ | $n_D^{20}$ = 1.5528 |
| 21 | | | | | 89–95 |
| 22 | • $NH_4$ | $OCH_3$ | $OCH_3$ | $OCH_3$ | 135–140 |
| 23 | $N=C(CH_3)(CH_3)$ | $OCH_3$ | $OCH_3$ | $OCH_3$ | 114–117 |
| 24 | $N=C(C_2H_5)(C_2H_5)$ | $OCH_3$ | $OCH_3$ | $OCH_3$ | 121–122 |
| 25 | $N=C(C_3H_7)(C_3H_7)$ | $OCH_3$ | $OCH_3$ | $OCH_3$ | 112–114 |
| 26 | $N=C(C_3H_7)(C_3H_7)$ | $OCH_3$ | H | H | $n_D^{20}$ = 1.5571 |

Among the compounds of the present invention, benzoic acid derivatives wherein R is a hydrogen atom, or their salts exhibit particularly excellent herbicidal effects.

Compound Nos. 1, 17, 18, 19, 20, 21 and 22 are particularly superior in that they have excellent herbicidal activities and no substantial phytotoxicity against crop plants, particularly rice and wheat.
The compounds of the present invention can be prepared in accordance with the following processes.
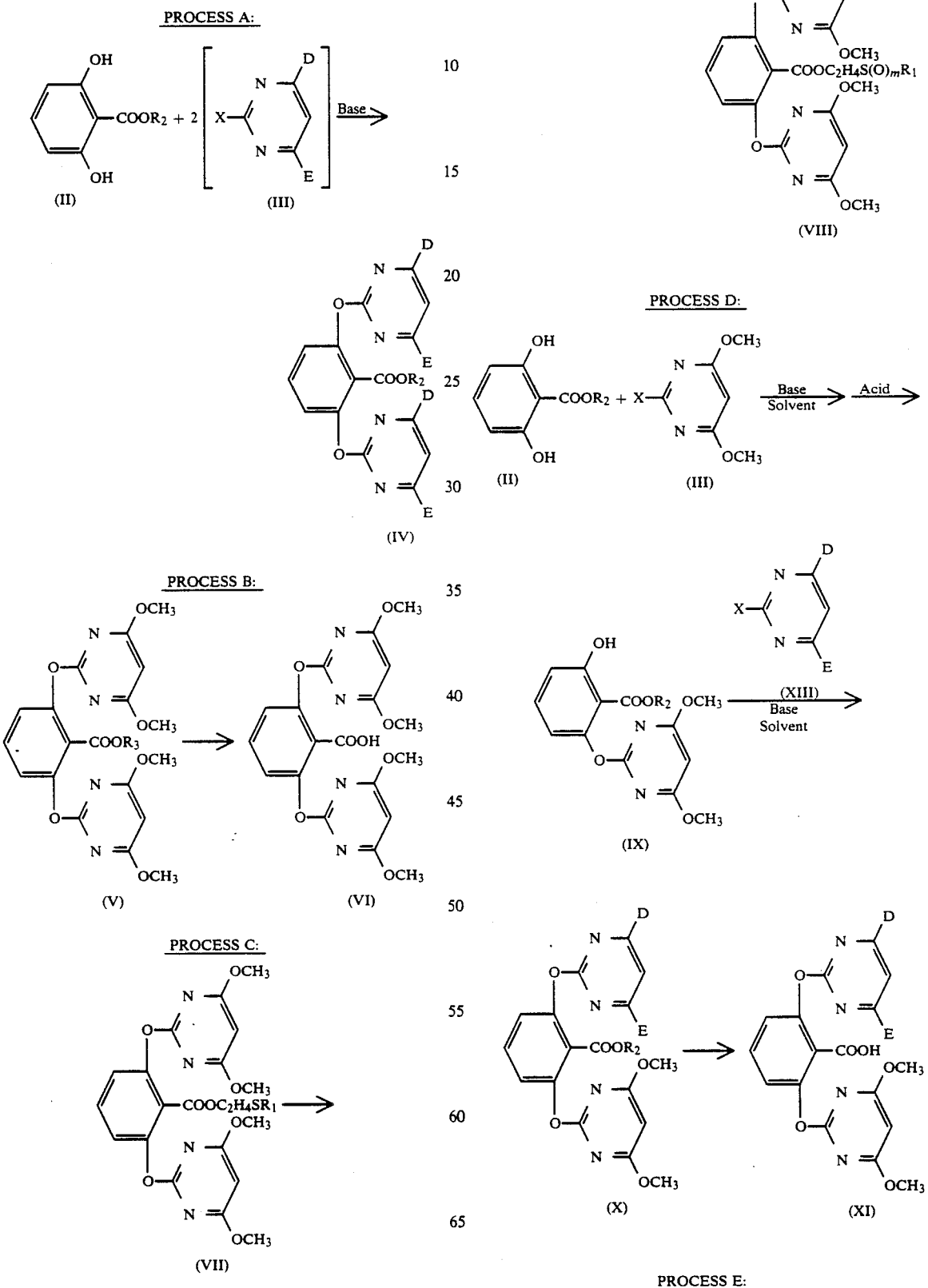

-continued

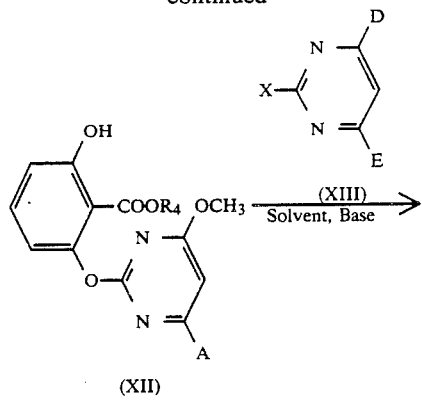

(XII)

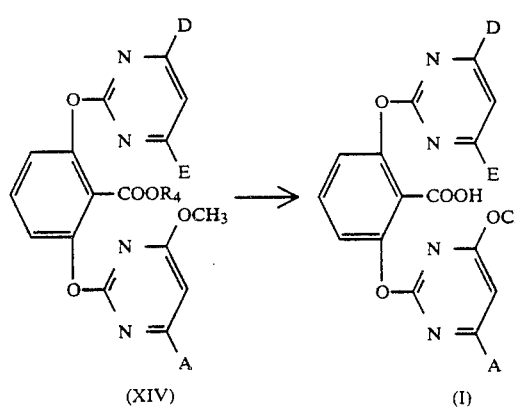

(XIV) → (I)

PROCESS F:

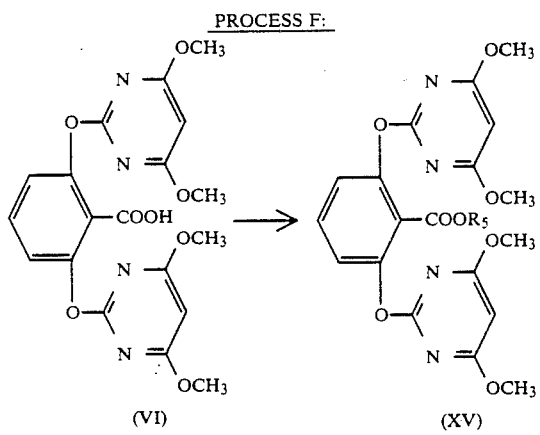

(VI) → (XV)

In the above formulas, $R_1$ is a lower alkyl group, $R_2$ is a hydrogen atom, a lower alkylthioethyl group, a benzyl group or a methoxybenzyl group, $R_3$ is a benzyl group or a methoxybenzyl group, $R_4$ is a benzyl group, methoxybenzyl group, or a trimethylsilyl group, $R_5$ is

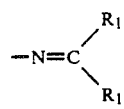

(wherein $R_1$ is as defined above) or —CH$_2$CH$_2$SR$_1$ (wherein $R_1$ is as defined above), X is a halogen atom, an alkylsulfonyl group or a benzylsulfonyl group, A, D and E are as defined above, and m is 1 or 2.

The 2,6-dihydroxybenzoic acid ester of the formula II can be prepared by reacting 2,6-dihydroxybenzoic acid with a halogenated alkane in the presence of a base preferably in a solvent, or by reacting an alcohol with a condensing agent such as carbonyl diimidazole preferably in a solvent.

Process A

The compound of the formula VI can be prepared by reacting the compound of the formula II with the compound of the formula III in the presence of at least 2 equivalent of a base in a solvent at a temperature within a range of from room temperature to the boiling point of the solvent for from 0.5 to 48 hours. As the base, an alkali metal such as sodium metal, potassium metal, an alkali metal hydride or alkaline earth metal hydride, such as potassium hydride or calcium hydride, an alkali metal carbonate such as sodium carbonate or potassium carbonate, or an organic amine such as triethylamine or pyridine may be employed.

As the solvent, a hydrocarbon solvent such as benzene, toluene or xylene, a halogenated hydrocarbon solvent such as methylene chloride or chloroform, an alcohol solvent such as methanol, ethanol or 2-propanol, an ether solvent such as diisopropyl ether, tetrahydrofuran or dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, acetonitrile, water or a mixture thereof, may be used.

The molar ratios of the compound of the formula II and the compound of the formula III are preferably one equivalent of the former and two equivalent of the latter. However, the compound of the formula VI can be prepared even when the compound of the formula II or the compound of the formula III is excessive within a range of from 1.1 to 1.2 times.

PROCESS B

A compound of the formula I wherein R is a hydrogen atom can be prepared by the reaction in accordance with Process A using at least three equivalent of a base, followed by acidification.

Further, it can also be prepared from a compound of the formula V by catalytic reduction with hydrogen.

PROCESS C

A compound of the formula I wherein R is —CH$_2$CH$_2$S(O)$_m$R$_1$ wherein R$_1$ is as defined above, and m is an integer of 1 or 2, can be prepared by oxidizing the compound of the formula VII in a solvent by means of an oxidizing agent.

PROCESS D

Then, a compound of the formula IX can be prepared by reacting one equivalent of the compound of the formula II and one equivalent of the compound of the formula III. Then, after isolating it or without isolating it, a compound of the formula X can be prepared. From the compound of the formula X, a compound of the formula XI can be prepared in accordance with Process B.

PROCESS E

A compound of the formula XIV is prepared from the compounds of the formulas XII and XIII in accordance with Process A or D. When R$_4$ is a trimethylsilylethyl group, it is reacted with tetrabutylammoniumfluoride trihydrate to obtain a compound of the formula I.

PROCESS F

The compound of the formula VI is imidazolyl-modified or halogenated with carbonyl diimidazole, thionyl chloride, oxalic acid chloride or phosgene, followed by a reaction with dialkylketone oxime to obtain a compound of the formula XV.

2,6-bis[(4,6-dimethoxypyrimidine-2-yl)oxy]benzoic acid thus prepared, can be converted to its alkali metal salt by reacting it with an equal amount of sodium bicarbonate, sodium hydroxide, potassium hydroxide or sodium hydride.

Then, the alkali metal salt may be reacted with calcium chloride or the corresponding benzoic acid is reacted with calcium carbonate or calcium hydride, to obtain an alkaline earth metal salt. Further, the alkali metal salt may be reacted with iron chloride to obtain a transition metal salt such as an iron salt.

Further, it is possible to convert the benzoic acid to an organic ammonium salt by reacting it with an aliphatic amine such as a primary amine, a secondary amine, a tertiary amine, diethanol amine, triethanol amine, an alkoxyalkylamine, a cyclohexylamine or morphorine, or with an aromatic amine such as aniline or naphthylamine.

Now, the present invention will be described in further detail with reference to Examples. However, it should be understood that the present invention is by no means restricted to such specific Examples.

EXAMPLE 1

Preparation of isopropylammonium 2,6-bis[(4,6-yl)oxy]benzoic acid (Comoound No. 1)

2.0 g (3.8 mmol) of benzyl 2,6-bis[(4,6-dimethoxypyrimidin-2-yl)oxy]benzoate (melting point: 130–132° C.) was dissolved in methanol. The solution was added to 0.3 g of 10% palladium-carbon preliminarily wetted with acetic acid and methanol. Hydrogen was introduced under atmospheric pressure to conduct catalytic reduction. When absorption of hydrogen ceased the reaction was regarded as terminated, and the reaction solution was subjected to filtration. The filtrate was concentrated under reduced pressure. Then, to the residue, ethyl acetate and water were added for liquid separation. The ethyl acetate layer was washed with water, dried and concentrated. Crystals thereby obtained were washed with hexane to obtain 1.0 g of a white powder having a melting point of from 148 to 150° C.

EXAMPLE 2

Preparation of 2,6-bis[(4,6-dimethoxypyrimidin-2-yl)oxy]benzoic acid (Compound No. 1)

By using 5.5 g (10 mmol) of 4-methoxybenzyl 2,6-bis[(4,6-dimethoxypyridin-2-yl)oxy]benzoate (melting point: 82–83° C.), the operation was conducted in the same manner as in Example 1 to obtain 3.0 g of the desired compound as a white powder having a melting point of from 148 to 150° C.

EXAMPLE 3

Preparation of 2-ethylsulphenylethyl 2,6-bis[(4,6-dimethoxypyrimidin-2-yl)oxy]benzoate (Compound No. 4)

24.0 g (46.3 mmol) of 2-ethylthioethyl 2,6-bis[(4,6-dimethoxypyrimidin-2-yl)oxy]benzoate was dissolved in chloroform. Then, a chloroform solution prepared by dissolving 8.8 g of m-chloroperbenzoate under cooling with ice, was dropwise added thereto at a temperature of from 5 to 10° C. The mixture was reacted at the same temperature for one hour. Then, an aqueous sodium sulfite solution was added thereto, and the mixture was subjected to liquid separation. The organic layer was washed with an aqueous sodium bicarbonate solution, dried and concentrated to obtain 23.5 g of a slightly brown viscous substance. This substance was solidified, and the solid showed a melting point of from 88 to 90° C.

EXAMPLE 4

Preparation of 2-(4-chloro-6-methoxypyrimidin-2-yl)oxy-6-(4,6-dimethoxypyrimidin-2-yl)oxybenzoic acid (Compound No. 6)

1) Preparation of trimethylsilylethyl 2-(4-chloro-6-methoxypyrimidin-2-yl)oxy-6-(4,6-dimethoxypyrimidin-2-yl)oxybenzoate NaH (0.4 g, purity: 60%) was suspended in 50 ml of THF. To this suspension, trimethylsilylethyl 6-(4,6-dimethoxypyrimidin-2-yl)oxysalicylate (3.0 g) was added, and the mixture was stirred at room temperature for 30 minutes. To this mixture, 4-chloro-6-methoxy-2-methylsulfonylpyrimidine (1.8 g) was added, and the mixture was stirred at room temperature for further 12 hours. After completion of the reaction, water was added thereto, and the mixture was extracted with ethyl ether. The ethyl ether layer was dried over anhydrous magnesium sulfate. Then, the solvent was distilled off under reduced pressure. The crude extract thus obtained was purified by silica gel column chromatography to obtain the above identified compound as a slightly yellow liquid (4.0 g).

2) Preparation of 2-(4-chloro-6-methoxypyrimidin-2-yl)oxy-6-(4,6-dimethoxypyrimidin-2-yl)oxybenzoic acid Trimethylsilylethyl 2-(4 chloro 6-methoxypyrimidin-2-yl)oxy-6-(4,6-dimethoxypyrimidin-2-yl)oxybenzoate (4.0 g) was dissolved in 30 ml of DMF. To this solution, tetrabutylammonium fluoride trihydrate (5.9 g) was added, and the mixture was stirred at room temperature for 15 minutes. After completion of the reaction, water and a small amount of an aqueous potassium hydrogen sulfate solution were added thereto, and the mixture was extracted with ethyl acetate. The organic layer was washed with a saturated sodium chloride aqueous solution and then dried over anhydrous magnesium sulfate. The solvent was distilled off under reduced pressure, and the crystals thereby obtained were washed with a mixture of hexane and IPE to obtain the above identified compound as white crystals (3.2 g). (Melting point: 150–152° C.)

EXAMPLE 5

Preparation of isopropylammonium 2,6-bis[(4,6-dimethoxypyrimidin-2-yl)oxy]benzoate (Compound No. 17)

2,6-bis[(4,6-dimethoxypyrimidin-2-yl)oxy]benzoic acid (2.0 g) and isopropylamine (1.0 g) were dissolved in 30 ml of THF, and the mixture was stirred at room temperature for 12 hours. The reaction solution was concentrated, and crystals thereby precipitated, were washed with hexane to obtain the above identified compound as white crystals (1.9 g). (Melting point: 99–102° C.)

EXAMPLE 6

Preparation of isopropylidene aminoester of 2,6-bis[(4,6-dimethoxypyrimidin 2-yl)oxy]benzoic acid (Compound No. 23)

2,6-bis[(4,6-dimethoxypyrimidin-2-yl)oxy]benzoic acid (3.0 g) and N,N'-carbonyldiimidazole (1.2 g) were dissolved in 50 ml of THF, and the solution was refluxed under heating for 15 minutes. To this reaction solution, acetone oxime (0.6 g) was added, and the mixture was refluxed under heating for further 16 hours.

After completion of the reaction, water was added thereto, and the mixture was extracted with ethyl acetate. The organic layer was washed with a saturated sodium chloride aqueous solution and dried over anhydrous magnesium sulfate. Then, the solvent was distilled off under reduced pressure. The crude extract thus obtained was purified by silica gel column chromatography to obtain the above identified compound as white crystals (2.1 g). (Melting point: 114–117° C.)

EXAMPLE 7

Preparation of tris(2-hydroxyethyl)ammonium 2,6-bis[(4,6-dimethoxypyrimidin-2-yl)oxy]benzoate (Compound No. 19)

2,6-bis[(4,6-dimethoxypyrimidin-2-yl)oxy]benzoic acid (2.0 g) and triethanolamine (0.7 g) were dissolved in 30 ml of THF, and the solution was stirred at room temperature for 12 hours.

The reaction solution was concentrated, and crystals thereby precipitated were washed with hexane to obtain the above identified compound as white crystals (2.4 g). (Melting point: 103–110° C.)

EXAMPLE 8

Ammonium 2,6-bis[(4,6-dimethoxypyrimidin-2-yl)oxy]benzoate (Compound No. 22)

2,6-bis[(4,6-dimethoxypyrimidin-2-yl)oxy]benzoic acid (5.1 g) and 28% aqueous ammonia (1.7 g) were mixed with a solvent mixture of THF/ethanol. Precipitated crystals were washed with acetone to obtain the above .drentified compound as white crystals (3.7 g). (Melting point: 135–140° C.

EXAMPLE 9

Preparation of methylthioethyl 2,6-bis[(4,6-dimethoxypyrimidin-2-yl)oxy]benzoate (Compound No. 2)

Methylthioethyl 2,6-dihydroxybenzoate (4.5 g) was dissolved in DMF, and 60% sodium hydride (1.6 g) was added thereto. Then, 2-chloro-4,6-dimethoxypyrimidine (3.5 g) was added thereto, and the mixture was heated and reacted at a temperature within a range of from 90 to 110° C. for two hours. The reaction solution was poured into ice water and then extracted twice with ethyl acetate. The ethyl acetate layer was washed with water and dried over anhydrous sodium sulfate. After removing inorganic substances by filtration, the solvent was distilled off under reduced pressure. The residue was purified by column chromatography to obtain the above identified compound as a colorless viscous liquid. ($\eta^{20}_D$.1.5706).

EXAMPLE 10

Preparation of 2,6-bis[(4,6-dimethoxycvrimidin-2-yl)oxy]benzoic acid (Compound No. 1)

60% sodium hydride (1.4 g) was suspended in THF. To the suspension, benzyl 2,6-dihydroxybenzoate (8.0 g) was added, and the mixture was stirred at room temperature for 15 minutes. Then, 4,6-dimethoxy-2-methylsulfonyl pyrimidine (7.8 g) was added thereto, and the mixture was reacted for 8 hours under reflux.

After cooling, the reaction solution was poured into water and extracted with ethyl ether. The organic layer was washed with a saturated sodium chloride aqueous solution and dried over anhydrous magnesium sulfate. The solvent was distilled off under reduced pressure. The residue was purified by silica gel column chromatography to obtain benzyl 6-(4,6-dimethoxypyrimidin-2-yl)oxysalicylate (2.0 g) as white crystals. (Melting point: 63–65° C.)

Benzyl 6-(4,6-dimethoxypyrimidin-2-yl)oxysalicylate thus obtained, was reacted with 4,6-dimethoxy-2-methylsulfonylpyrimidine in the same manner as in Example 4 to obtain benzyl 2,6-bis[(4,6-dimethoxypyrimidin-2-yl)oxy]benzoate (Melting point: 130–132° C. as white needle-like crystals).

Benzyl 2,6-bis[(4,6-dimethoxypyrimidin-2-yl)oxy]benzoate thus obtained, was hydrolyzed in the same manner as in Example 1 to obtain 2,6-bis[(4,6-dimethoxypyrimidin-2-yl)oxy]benzoic aicd as a white powder. (Melting point: 148–150° C.)

EXAMPLE 11

Preparation of 2,6-bis{[[4-chloro-6-methoxy)pyrimidin-2-yl]oxy}benzoic acid (Compound No. 12)

60% sodium hydride (1.6 g) was suspended in THF. To the suspension, 2,6-dihydroxybenzoic acid (2.0 g) was added, and the mixture was stirred at room temperature for 30 minutes. Then, 4-chloro-6-methoxy-2-methylsulfonylpyrimidine (5.8 g) was added thereto, and the mixture was reacted at room temperature for two days.

After the reaction, the reaction solution was poured into water and extracted with ethyl acetate. The organic layer was washed with a saturated sodium chloride aqueous solution and dried over anhydrous sodium sulfate. The solvent was distilled off under reduced pressure. The residue was purified by column chromatography to obtain the above identified compound (1.6 g) as slightly yellow crystals. (Melting point: 149–150° C.)

The herbicidal composition of the present invention comprises a herbicidally effective amount of the compound of the present invention and an agricultural adjuvant. The herbicide of the present invention may be used as it is or may be formulated in various formulations such as a wettable powder, a granule, an emulsifiable concentrate or a dust by blending it in an amount of from 0.5 to 95 parts by weight, preferably from 1 to 80 parts by weight, with a carrier, a surfactant, a dispersing agent or an adjuvant which is commonly employed for the formulation of agricultural chemicals, in an amount to make up the total of 100 parts by weight.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned.

The proportion of the compound of the present invention in the formulation may vary depending upon the type of the formulation, the application method, the application site, timing, etc. Therefore, it can not generally be defined. However, it is usually from 5 to 90% by weight in a wettable powder, from 5 to 80% by weight in an emulsifiable concentrate, from 1 to 60% by weight in a flowable, from 0.5 to 20% by weight in a granule, from 5 to 40% by weight in a liquid formulation, from 0.5 to 10% by weight in a dust and from 5 to 90% by weight in a dry flowable.

A liquid formulation can be prepared either by using the active ingredient in the form of a salt, or by adding a basic substance to the active ingredient in the form of an acid at the time of formulation. In practical use, such a herbicide may be diluted to a suitable concentration before application, or may directly be applied.

The herbicide of the present invention is capable of controlling various weeds in an agricultural field such as an upland field or an orchard, or in a forest, a lawn or other non-agricultural field by soil treatment before or after the emergence of weeds or by foliage treatment. Further, the herbicide is capable of controlling various weeds in a paddy field by irrigated soil treatment before or after the emergence of weeds or by foliage treatment.

For soil treatment, the herbicide of the present invention is applied in a dose of from 0.1 g to 1 kg, preferably from 0.5 to 500 g, more preferably from 1 to 100 g, of the active ingredient per 10 ares. For foliage treatment, it is diluted to a concentration of from 1 to 10,000 ppm for application. Most preferably, it is applied in a dose of from 1 to 10 g of the active ingredient per 10 ares for a paddy field, in a dose of from 5 to 50 g per 10 ares for an orchard or a lawn, and in a dose of from 10 to 100 g for a forest or a nonagricultured field.

Now, Formulation Examples for the herbicidal composition of the present invention will be given. However, it should be understood that the present invention is by no means restricted to these specific Examples. In these Examples, "%" means "% by weight".

FORMULATION EXAMPLE 1 wettable powder

10% of Compond No. 1, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (trademark, Jeeklite Company Ltd.) were uniformly mixed and pulverized to obtain a wettable powder.

FORMULATION EXAMPLE 2 emulsifiable concentrate

30% of Compound No. 1, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3 granule

5% of Compound No. 1, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 dust

2% of Compound No. 2, 5% of diatomaceous earth and 93% of clay were uniformly mixed and pulverized to obtain a dust.

The compounds and the herbicidal compositions of the present invention are capable of effectively controlling annual weeds such as barnyardgrass (*Echinochloa crusqalli*), crabgrass (*Digitaria sanguinalis*), goosegrass (*Eleusine indica*), green foxtail (*Setaria viridis*), water foxtail (*Alopecurus aegualis*), annual bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenopodium album*), velvetleaf (*Abutilon theophrasti*), prickly sida (*Sida spinosa*), sicklepod (*Cassia tora*), chickweed (*Stellaria media*), morningglory (*Ipomea spp*), common cocklebur (*Xanthium strumarium*), rice flatsedge (*Cyperus iria*), broadleaf signalgrass (*Brachiaria platyphylla*), itchgrass (*Rottoboelia exaltata*), downy brome (*Bromus tectorum*), wild buckwheat (*Polygonum convolvulus*), wild mustard (*Brassica aryensis*) and devils beggarticks (*Bidens frondosa*), and perennial weeds such as purple nutsedge (*Cyperus rotundus*), johnsongrass (*Sorghum halepense*), bermudagrass (*Cynodon dactylon*) and quackgrass (*Agropyron repens*) grown in upland fields including agricultural fields, orchards and nonagricultural fields.

Further, they are capable of effectively controlling annual weeds such as barnyardgrass (*Echinochloa crusgalli*), flatsedge (*Cyperus difformis*), monochoria (*Monochoria vaqinalis*), and perennial weeds such as bulrush (*Scirpus hotarui*) Alisma canaliculatum, Cyperus serotinus, Sagittaria pyqmaea and Eleocharis kuroquwai, grown in paddy fields. Furthermore, as herbicides for lawns, they are capable of controlling annual weeds such as crabrass (*Digitaria sanguimalis*), annual bluegrass (*Poa annua*) and creeping woodsorrel (*Oxalis corniculata*), and perennial weeds such as purple nutsedge (*Cyperus rotundus*) grown in golf fields or gardens. They are also capable of controlling perennial weeds such as kudzu (*Pueraria thunbergiana*), Japanese plume grass (*Miscanthus sinensis Anderss*) and bamboo grass (Pleiblastus spp.) grown in forests.

Now, the herbicidal activities of the herbicides of the present invention will be described with reference to Test Examples.

The compounds of the present invention have the following features:

(1) They have high herbicidal effects, and they are very effective at a low dose.

(2) They are highly effective in soil treatment before emergence. However, they are particularly effective in foliage treatment after emergence.

(3) They have a wide herbicidal spectrum. (They are effective not only against annual weeds belonging to rice, broadleaf or cyperaceous weed family, but also perennial weeds belonging to rice, broadleaf or cyperaceous weed family.

(4) They have a high level of safety to crop plants. Particularly, they are highly safe to rice, wheat and lawn. They can safely be used also for transplanted paddy field rice.

(5) They are herbicidally highly effective even against weeds of a highly advanced leafstage (i.e. highly grown weeds).

(6) They do not remain in soil and give no adverse effects to rotated crops.

(7) They have no substantial toxicity against mammal or fish and have a high level of safety thereto.

Now, the herbicidal activities of the herbicides of the present invention will be described with reference to Test Examples.

The following abbreviations represent the following test plants:
Or: rice, Tr: wheat, EC: barnyardgrass,
Se: green foxtail, Po: smartweed, Am: slender amaranth, Ip: morningglory, Xa: common cocklebur,
Cr: purple nutsedge, Di: crabgrass,
Ch: lambsquarters, Ci: rice flatsedge, Cd: flatsedge,
Mo: monochoria, Sc: bulrush, So: Johnsongrass,
Al water foxtail and Ab: velvetleaf

TEST EXAMPLE 1 foliage tretment in upland field

In a pot filled with soil (surface area: 100 cm$^2$), seeds of barnyardgrass (Ec), crabgrass (Di), smartweed (Po), slender amaranth (Am), lambsquarters (Ch) and rice flatsedge (Ci), were sown and covered with soil in a thickness of from 0.5 to 1 cm. The pot was cultured in a green house at a temperature of from 20 to 25° C. for 2 weeks, and then a predetermined amount of a wettable powder prepared in accordance with Formulation Example 1 was diluted with water, and applied to the foliage at a rate of 100 liters per 10 ares (dose of active ingredient: 400 g/10 ares). The evaluation was conducted on the 14th day after the treatment in accordance with the standard as identified in Table 2. The results are shown by the index numbers in Table 3.

TABLE 2

| Index No. | Herbicidal effects and Phytotoxicity |
| --- | --- |
| 0 | No herbicidal effect (or no phytotoxicity) |
| 1 | Herbicidal effect (or phytotoxicity): more than 0% and less than 30% |
| 2 | Herbicidal effect (or phytotoxicity): at least 30% and less than 50% |
| 3 | Herbicidal effect (or phytotoxicity): at least 50% and less than 70% |
| 4 | Herbicidal effect (or phytotoxicity): at least 70% and less than 90% |
| 5 | Herbicidal effect (or phytotoxicity): more than 90% |

TABLE 3

| Compound No. | Herbicidal effects | | | | | |
| --- | --- | --- | --- | --- | --- | --- |
|  | Ec | Di | Po | Am | Ch | Ci |
| 1 | 5 | 5 | 5 | 5 | 5 | 5 |
| 2 | 5 | 5 | 5 | 5 | 5 | 5 |

TABLE 3-continued

| Compound No. | Herbicidal effects | | | | | |
| --- | --- | --- | --- | --- | --- | --- |
|  | Ec | Di | Po | Am | Ch | Ci |
| 3 | 4 | 4 | 4 | 5 | 5 | 2 |
| 4 | 5 | 5 | 5 | 5 | 4 | 4 |
| 5 | 5 | 5 | 5 | 5 | 4 | 4 |
| 6 | 5 | 5 | 4 | 5 | 5 | 5 |
| 8 | 5 | 5 | 5 | 5 | 5 | 5 |
| 11 | 5 | 4 | 5 | 5 | 5 | 5 |
| 14 | 5 | 5 | 5 | 5 | 4 | 5 |
| 16 | 5 | 4 | 5 | 5 | 5 | 5 |
| 17 | 5 | 5 | 5 | 5 | 5 | 5 |
| 18 | 5 | 5 | 5 | 5 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |
| 22 | 5 | 5 | 5 | 5 | 5 | 5 |
| 23 | 5 | 5 | 5 | 5 | 5 | 5 |
| 24 | 5 | 5 | 5 | 5 | 5 | 5 |
| 25 | 5 | 5 | 5 | 5 | 5 | 5 |
| 26 | 5 | 5 | 5 | 5 | 4 | 5 |

TEST EXAMPLE 2 soil treatment in upland field

In a pot filled with soil (surface area: 100 cm$^2$), seeds of barnyardgrass (Ec), crabgrass (Di), smartweed (Po), slender amaranth (Am), lambsquarters (Ch) and rice flatsedge (Ci) were sown and covered with soil in a thickness of from 0.5 to 1 cm. One day later from the seeding, a predetermined amount of a wettable powder prepared in accordance with Formulation Example 1, was diluted with water and applied to the soil surface at a rate of 100 liters per 10 ares (dose of active ingredient 400 g/10 ares). The evaluation was conducted on the 20th day after the treatment in accordance with the standard as identified in Table 2. The results are shown by the index numbers in Table 4.

TABLE 4

| Compound No. | Herbicidal effects | | | | | |
| --- | --- | --- | --- | --- | --- | --- |
|  | Ec | Di | Po | Am | Ch | Ci |
| 1 | 5 | 5 | 5 | 5 | 5 | 5 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 10 | 5 | 4 | 5 | 5 | 5 | 5 |
| 11 | 5 | 5 | 5 | 5 | 5 | 5 |
| 12 | 5 | 4 | 5 | 5 | 5 | 5 |
| 13 | 5 | 5 | 5 | 5 | 5 | 5 |
| 14 | 4 | 5 | 5 | 5 | 5 | 5 |
| 15 | 5 | 5 | 5 | 5 | 5 | 5 |
| 17 | 5 | 5 | 5 | 5 | 5 | 5 |
| 18 | 5 | 5 | 5 | 5 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |
| 22 | 5 | 5 | 5 | 5 | 5 | 5 |
| 23 | 5 | 5 | 5 | 5 | 5 | 5 |
| 24 | 5 | 5 | 5 | 5 | 5 | 5 |
| 25 | 5 | 5 | 5 | 5 | 5 | 5 |

TEST EXAMPLE 3 test of controlling weeds in paddy field

In a pot filled with paddy field soil (surface area: 100 cm$^2$), seeds of barnyardgrass (Ec), flatsedge (Cd), monochoria (Mo) and bulrush (Sc) were sown, and water was introduced to a depth of 3 cm. Two days later from the seeding, a predetermined amount of wettable powder prepared in accordance with Formulation Example 1, was diluted with water and dropwise applied to the water surface in a dose of 100 g of the active ingredient per 10 ares. The evaluation was conducted on the 21st day after the treatment in accordance with the standard as identified in Table 2. The results are shown by the index numbers in Table 5.

TABLE 5

| Compound | Herbicidal effects | | | |
|---|---|---|---|---|
| No. | Ec | Cd | Mo | Sc |
| 1 | 5 | 5 | 5 | 5 |
| 2 | 5 | 5 | 5 | 5 |
| 3 | 4 | 5 | 5 | 5 |
| 4 | 4 | 5 | 5 | 4 |
| 5 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 11 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 5 | 5 | 5 | 5 |
| 16 | 5 | 5 | 5 | 5 |
| 17 | 5 | 5 | 5 | 5 |
| 18 | 5 | 5 | 5 | 5 |
| 19 | 5 | 5 | 5 | 5 |
| 20 | 5 | 5 | 5 | 5 |
| 21 | 5 | 5 | 5 | 5 |
| 22 | 5 | 5 | 5 | 5 |
| 23 | 5 | 5 | 5 | 5 |
| 24 | 5 | 5 | 5 | 5 |
| 25 | 5 | 5 | 5 | 5 |

TEST EXAMPLE 4 selective herbicidal test

In a pot filled with soil (surface area: 600 cm$^2$), seeds of rice (Or), wheat (Tr), barnyardgrass (Ec), green foxtail (Se), smartweed (Po), slender amaranth (Am), morningglory (Ip) and common cocklebur (Xa) were sown, tubers of purple nutsedge (Cr) were planted and covered with soil in a thickness of from 0.5 to 1 cm. The pot was cultured in a green house at a temperature of from 20 to 25° C. for 2 weeks, and then, a predetermined amount of a wettable powder prepared in accordance with Formulation Example 1 was diluted with water, and applied to the foliage at a rate of 100 liters per 10 ares. The evaluation was conducted on the 30th day after the treatment in accordance with the standard as identified in Table 2. The results are shown by the index numbers in Table 6.

TABLE 6

| Compound No. | Dose of active ingredient (g/10a) | Phytotoxicity | | Herbicidal effects | | | | | | |
|---|---|---|---|---|---|---|---|---|---|---|
| | | Or | Tr | Ec | Se | Po | Am | Ip | Xa | Cr |
| 1 | 25 | 0 | 0 | 5 | 5 | 5 | 5 | 5 | 5 | 5 |
| | 6.3 | 0 | 0 | 4 | 5 | 5 | 5 | 4 | 5 | 4 |
| 4 | 400 | 0 | 0 | 5 | 5 | 5 | 5 | 4 | 5 | 2 |
| | 100 | 0 | 0 | 3 | 5 | 5 | 5 | 2 | 5 | 1 |
| 5 | 400 | 0 | 0 | 5 | 4 | 5 | 5 | 4 | 5 | 3 |
| | 100 | 0 | 0 | 4 | 2 | 5 | 4 | 3 | 5 | 2 |

TEST EXAMPLE 5 foliage treatment—herbicidal test

In a pot filled with soil (surface area: 600 cm$^2$), barnyardgrass (Ec), crabgrass (Di), green foxtail (Se), Johnsongrass (So), smartweed (Po), slender amaranth (Am), velvetleaf (Ab), morningglory (Ip) and common cocklebur (Xa) were sown and covered with soil in a thickness of from 0.5 to 1 cm. The pot was cultured in a green house at a temperature of from 20 to 30° C. for ten days, and then, a predetermined amount of a wettable powder prepared in accordance with Formulation Example 1 was diluted with water containing an extender, and applied to the foliage at a rate of 100 liters per 10 ares. The evaluation was conducted on the 21st day after the treatment in accordance with the standard as identified in Table 2. The results are shown by the index numbers in Table 7.

TABLE 7

| Compound No. | Dose of active ingredient (g/10a) | Herbicidal effects | | | | | | | | |
|---|---|---|---|---|---|---|---|---|---|---|
| | | Ec | Di | Se | So | Po | Am | Ab | Ip | Xa |
| 1 | 6.3 | 5 | 5 | 5 | 5 | 5 | 5 | 5 | 5 | 5 |
| | 1.6 | 5 | 4 | 5 | 5 | 5 | 5 | 4 | 5 | 5 |
| 6 | 6.3 | 5 | 4 | 5 | 5 | 4 | 5 | 5 | 5 | 5 |
| | 1.6 | 5 | 3 | 5 | 5 | 4 | 5 | 5 | 5 | 5 |
| 10 | 6.3 | 5 | 3 | 4 | 5 | 5 | 5 | 4 | 5 | 5 |
| | 1.6 | 5 | 2 | 3 | 5 | 5 | 5 | 3 | 4 | 4 |
| 14 | 6.3 | 4 | 3 | 4 | 5 | 5 | 5 | 2 | 5 | 5 |
| 17 | 6.3 | 5 | 5 | 5 | 5 | 5 | 5 | 5 | 5 | 5 |
| | 1.6 | 5 | 4 | 5 | 5 | 5 | 5 | 3 | 4 | 5 |
| 18 | 6.3 | 5 | 5 | 5 | 5 | 5 | 5 | 4 | 4 | 5 |
| | 1.6 | 5 | 3 | 5 | 5 | 5 | 5 | 3 | 5 | 5 |
| 19 | 6.3 | 5 | 5 | 5 | 5 | 5 | 5 | 5 | 5 | 5 |
| | 1.6 | 5 | 5 | 5 | 5 | 5 | 5 | 3 | 4 | 5 |
| 20 | 6.3 | 5 | 5 | 5 | 5 | 5 | 5 | 4 | 5 | 5 |
| | 1.6 | 5 | 4 | 5 | 5 | 5 | 5 | 3 | 3 | 5 |
| 21 | 6.3 | 5 | 5 | 5 | 5 | 5 | 5 | 4 | 5 | 5 |
| | 1.6 | 5 | 3 | 5 | 5 | 5 | 5 | 3 | 4 | 5 |
| 22 | 6.3 | 5 | 5 | 5 | 5 | 5 | 5 | 5 | 5 | 5 |
| | 1.6 | 5 | 4 | 5 | 5 | 5 | 5 | 4 | 5 | 5 |
| 23 | 6.3 | 4 | 3 | 4 | 4 | 5 | 5 | 5 | 5 | 5 |
| 24 | 6.3 | 5 | 2 | 4 | 5 | 5 | 5 | 3 | 3 | 5 |
| Comparative Compound No. | | | | | | | | | | |
| 1 | 6.3 | 0 | 0 | 0 | 0 | 0 | 3 | 1 | 0 | 0 |
| | 1.6 | 0 | 0 | 0 | 0 | 0 | 2 | 0 | 0 | 0 |
| 2 | 6.3 | 0 | 0 | 0 | 0 | 1 | 2 | 0 | 0 | 0 |
| | 1.6 | 0 | 0 | 0 | 0 | 1 | 0 | 0 | 0 | 0 |
| 3 | 6.3 | 0 | 0 | 0 | 0 | 2 | 4 | 1 | 0 | 0 |
| | 1.6 | 0 | 0 | 0 | 0 | 0 | 2 | 0 | 0 | 0 |
| 4 | 6.3 | 0 | 0 | 0 | 0 | 2 | 0 | 0 | 0 | 0 |
| | 1.6 | 0 | 0 | 0 | 0 | 0 | 0 | 0 | 0 | 0 |
| 5 | 6.3 | 0 | 0 | 0 | 0 | 4 | 4 | 2 | 2 | 2 |
| | 1.6 | 0 | 0 | 0 | 0 | 3 | 2 | 1 | 1 | 1 |

Comparative compounds 1, 2, 3, 4 and 5 (U.S. Pat. No. 4,248,619) will be identified below (the same applies in subsequent Tables):

Comparative Compound 1

1,3-bis(4,6-dimethyl-2-pyrimidinyloxy)benzene

Comparative Compound 2

1,3-bis(5-chloro-2-pyrimidinyloxy)-2-methylbenzene

Comparative Compound 3

1,3-bis(5-chloro-2-pyrimidinyloxy)-2-nitrobenzene

Comparative Compound 4

5-chloro-2-[3-(4,6-dimethyl-2-pyrimidinyloxy)-phenoxy]pyrimidine

Comparative Compound 5

1,2-bis(5-chloro-2-pyrimidinyloxy)benzene

TEST EXAMPLE 6 foliage treatment—phytotoxicity test to rice

In a pot filled with soil (surface area: 100 cm$^2$), seeds of rice (variety: Labelle) were sown and covered with soil in a thickness of 0.5 cm. The pot was cultured in a green house at a temperature of from 20 to 30° C. until 2.5 leaf stage, and then, a predetermined amount of a wettable powder prepared in accordance with Formulation Example 1 was diluted with water containing an extender, and applied to the foliage at a rate of 100 liters per 10 ares (dose of active ingredient: 6.3 g and 1.6 g per 10 ares). The phytotoxicity was evaluated on the 30th day after the treatment in accordance with the standard as identified in Table 2. As the results, no phytotoxicity was observed at either dose in the case of Compound Nos. 1, 10, 17, 18, 19, 20, 21 and 22 of the present invention.

TEST EXAMPLE 7 soil treatment—herbicidal test

In a pot filled with soil (surface area: 600 cm$^2$), seeds of barnyardgrass (Ec), greenfoxtail (Se), Johnsongrass (So) and water foxtail (Al) were sown and covered with soil in a thickness of from 0.5 to 1 cm. One day later from the seeding, a predetermined amount of a wettable powder prepared in accordance with Formulation Example 1 was diluted with water and applied to the soil surface at a rate of 100 liters per 10 ares. After the application, the pot was kept in a green house at a temperature of from 20 to 30° C. The evaluation was conducted on the 20th day after the treatment in accordance with the standard as identified in Table 2. The results are shown by the index numbers in Table 8.

TABLE 8

| | Dose of active ingredient (g/10a) | Herbicidal effects | | | |
|---|---|---|---|---|---|
| | | Ec | Se | So | Al |
| Compound No. | | | | | |
| 1 | 6.3 | 5 | 5 | 5 | 5 |
| 6 | 6.3 | 4 | 5 | 5 | 5 |
| 17 | 6.3 | 4 | 4 | 5 | 5 |
| 18 | 6.3 | 5 | 5 | 5 | 5 |
| 19 | 6.3 | 4 | 5 | 5 | 5 |
| 20 | 6.3 | 5 | 5 | 5 | 5 |
| 21 | 6.3 | 4 | 3 | 5 | 5 |
| 22 | 6.3 | 5 | 5 | 5 | 5 |
| 23 | 6.3 | 3 | 4 | 5 | 5 |
| 24 | 6.3 | 4 | 4 | 5 | 5 |
| Comparative Compound No. | | | | | |
| 1 | 6.3 | 0 | 0 | 0 | 0 |
| 2 | 6.3 | 0 | 0 | 1 | 0 |
| 3 | 6.3 | 0 | 0 | 0 | 0 |
| 4 | 6.3 | 0 | 0 | 0 | 0 |
| 5 | 6.3 | 0 | 0 | 1 | 0 |

TEST EXAMPLE 8 herbicidal test against purple nutsedge as perennial weed

In a pot filled with soil (surface are: 100 cm$^2$), tubers of purple nutsedge (Cr) were planted and covered with soil in a thickness of 1 cm. The pot was cultured in a green house at a temperature of from 20 to 30° C. until four leaf stage, and then, a predetermined amount of a wettable powder prepared in accordance with Formulation Example 1 was diluted with water containing an extender, and applied to the foliage. The evaluation was conducted on the 20th day after the treatment in accordance with the standard as identified in Table 2. The results are shown by the index numbers in Table 9.

TABLE 9

| | Dose of active ingredient (g/10a) | Herbicidal effects Cr |
|---|---|---|
| Compound No. | | |
| 1 | 25 | 5 |
| | 6.3 | 4 |
| 6 | 25 | 4 |
| | 6.3 | 4 |
| 7 | 25 | 4 |
| | 6.3 | 3 |
| 10 | 25 | 4 |
| | 6.3 | 3 |
| 11 | 25 | 4 |
| | 6.3 | 3 |
| 12 | 25 | 5 |
| | 6.3 | 4 |
| 14 | 25 | 4 |
| | 6.3 | 4 |
| 17 | 25 | 5 |
| | 6.3 | 4 |
| 18 | 25 | 5 |
| | 6.3 | 4 |
| 19 | 25 | 5 |
| | 6.3 | 5 |
| 20 | 25 | 5 |
| | 6.3 | 4 |
| 21 | 25 | 5 |
| | 6.3 | 4 |
| 22 | 25 | 5 |
| | 6.3 | 5 |
| 23 | 25 | 4 |
| | 6.3 | 4 |
| Comparative Compound No. | | |
| 1 | 25 | 0 |
| | 6.3 | 0 |
| 2 | 25 | 0 |
| | 6.3 | 0 |
| 3 | 25 | 0 |
| | 6.3 | 0 |
| 4 | 25 | 0 |
| | 6.3 | 0 |
| 5 | 25 | 0 |
| | 6.3 | 0 |

We claim:

1. A process for producing a pyrimidine derivative having the formula:

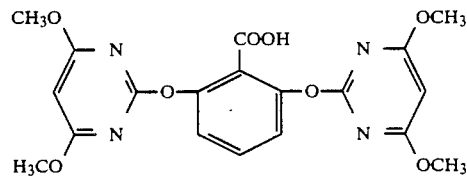

which comprises:

reacting 2,6-dihydroxybenzoic acid of the formula:

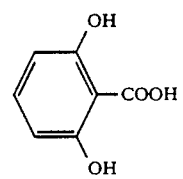

with a 2-substituted-4,6-disubstituted pyrimidine having the formula:

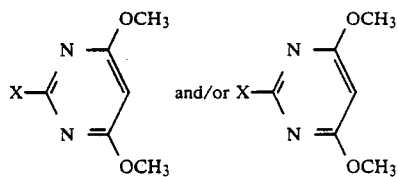
and/or
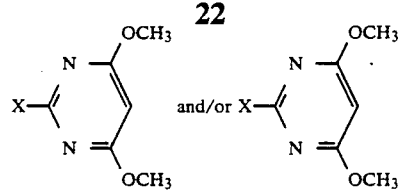
wherein X is a halogen atom, an alkylsulfonyl group, a benzylsulfonyl group or a substituted benzylsulfonyl group in the presence of NaH.
* * * * *
wherein X is a halogen atom, an alkylsulfonyl group, a benzylsulfonyl group or a substituted benzylsulfonyl group in the presence of NaH.
* * * * *